United States Patent [19]

Ferierabend

[11] Patent Number: 4,546,768

[45] Date of Patent: Oct. 15, 1985

[54] INHALATION APPARATUS FOR ANIMALS

[76] Inventor: Georg Ferierabend, Steinrain 25, Aarburg, Switzerland

[21] Appl. No.: 449,795

[22] Filed: Dec. 14, 1982

[30] Foreign Application Priority Data

Dec. 22, 1981 [CH] Switzerland ........................ 8188/81

[51] Int. Cl.[4] ..................... A61M 11/00; A61M 15/00

[52] U.S. Cl. .......................... 128/200.16; 128/204.11; 128/206.24; 128/207.13

[58] Field of Search ....................... 128/206.18, 200.16, 128/206.24, 204.13, 201.11, 203.29, 203.15, 201.23, 200.14, 205.25, 204.11, 204.12; 239/152, 153; 604/77

[56] References Cited

U.S. PATENT DOCUMENTS

| | | | |
|---|---|---|---|
| 3,812,854 | 5/1974 | Micheals et al. | 128/200.16 |
| 4,002,167 | 1/1977 | Rambosek | 128/206.24 |

FOREIGN PATENT DOCUMENTS

| | | | |
|---|---|---|---|
| 614012 | 2/1961 | Canada | 128/204.13 |
| 70703 | of 1942 | Czechoslovakia | 128/206.18 |
| 87054 | 6/1896 | Fed. Rep. of Germany | 128/206.18 |
| 315155 | 10/1919 | Fed. Rep. of Germany | 128/206.18 |
| 546106 | 3/1932 | Fed. Rep. of Germany | 128/206.18 |
| 582143 | 8/1933 | Fed. Rep. of Germany | 128/206.18 |
| 572329 | 6/1924 | France | 128/206.18 |
| 7308 | of 1897 | United Kingdom | 128/206.24 |
| 2107611 | 5/1983 | United Kingdom | 239/152 |

*Primary Examiner*—Henry J. Recla
*Assistant Examiner*—Karin M. Reichle
*Attorney, Agent, or Firm*—Flynn, Thiel, Boutell & Tanis

[57] ABSTRACT

An animal inhalation apparatus includes a mask which is directly fastened to a vaporizer. The baglike mask has a portion of its surface disposed in the mouth of a horse and is secured by a tightening belt so that the horse is prevented from opening its mouth and is forced to breath through its nostrils, which lie inside of the bag. The vaporizer operates in the rhythm of the breathing process. The horse is not connected to the vaporizer through a cumbersome hose, and only the respiratory organs are in contact with the inhalation medium.

9 Claims, 3 Drawing Figures

FIG. 1
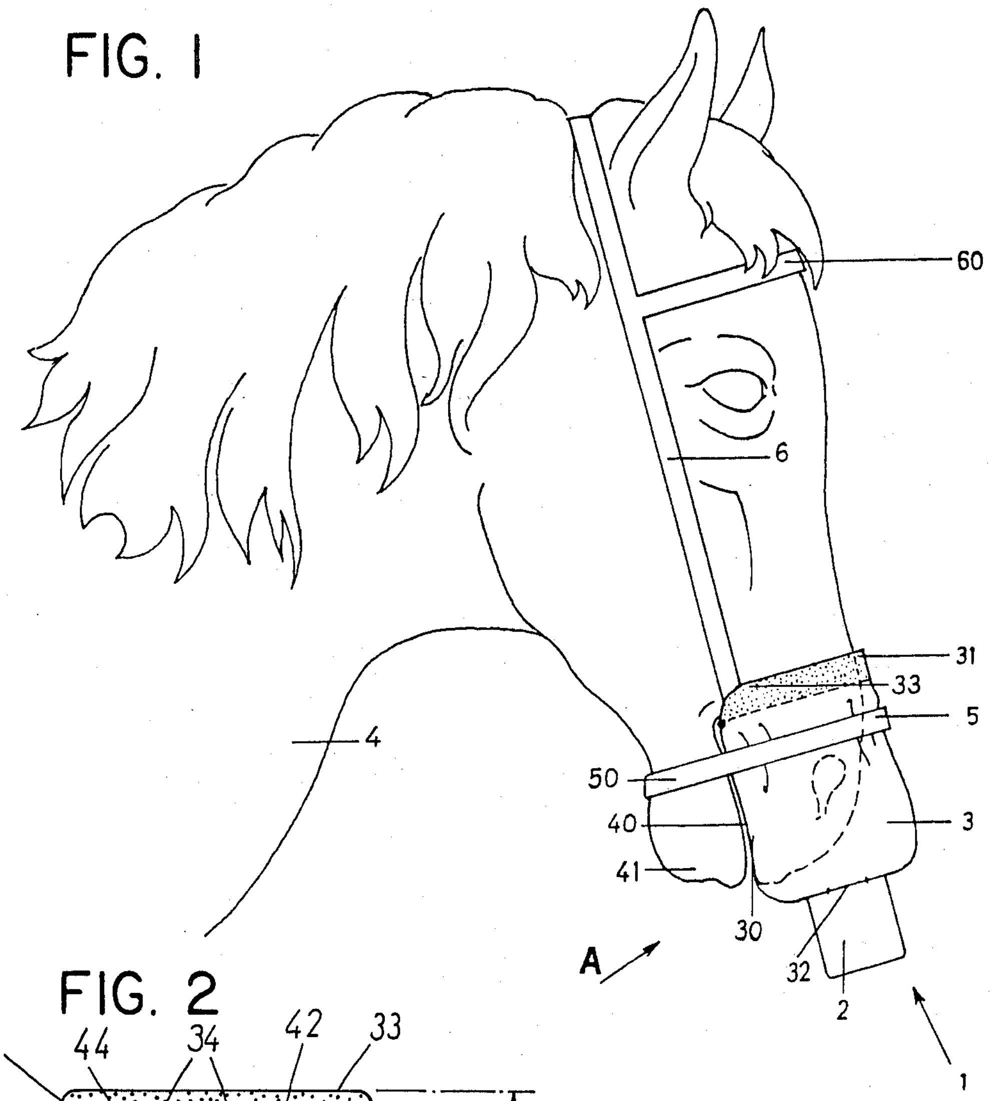
FIG. 2
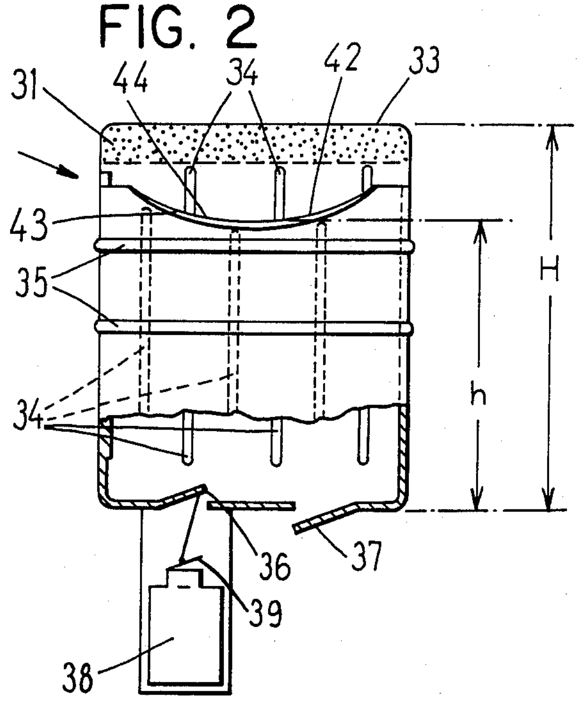
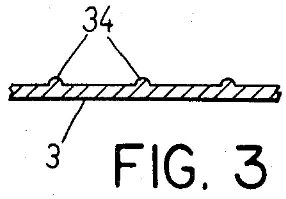
FIG. 3

INHALATION APPARATUS FOR ANIMALS

FIELD OF THE INVENTION

The invention relates to an inhalation apparatus with a mask adapted for use with animals, in particular horses.

BACKGROUND OF THE INVENTION

For the healing treatment of the respiratory organs, inhalation apparatuses are used, with which a suspension of solid or liquid particles in gases is inhaled. Such treatments are used both for humans and also for animals, whereby in the latter case there exists the difficulty of supplying the inhalation medium to the respiratory organs. Principally, two types of treatment can be used. The animal can either be held in a room which is saturated with the inhalation medium, or the medium can be supplied to the animal directly, for example through a tubular needle or by means of a head mask. Full head masks are known, which for the feeding of the air-steam mixture are connected by a hose to a vaporizer.

However, such a mask is impractical and has a disadvantage due to the needed hose length, since the atomized particles which are contained in the medium condense in the hose to droplets and thus do not enter the lungs of the animal.

SUMMARY OF THE INVENTION

A goal of the invention is therefore the provision of an inhalation apparatus which can be mounted simply and effectively on the head of an animal.

This is attained with an apparatus which includes a mask having a cylindrical portion and a flattened side which is adapted to be received in the mouth of the animal in a manner so that only the nose of the animal is covered, and having at least one tightening belt which extends around the cylindrical portion and the chin or lower jaw of the animal.

By moving a portion of the side or sleeve of the bag into the mouth of an animal, in particular a horse, only the outer respiratory organs are covered. In the case of horses, which are typically nose breathers, the nostrils are covered. In order to prevent breathing in through the mouth, the mouth of the animal is held closed by a belt fastening the mask on the animal.

In order that the full effect of the inhalation medium on the animal is not hindered by a hose, the vaporizer for producing the inhalation medium is arranged directly on the mask.

BRIEF DESCRIPTION OF THE DRAWING

FIG. 1 is a perspective view which illustrates an inventive inhalation apparatus on a horse;

FIG. 2 is a partly sectional view of the apparatus taken in the direction of arrow A in FIG. 1; and FIG. 3 is a fragmentary sectional view of a canvas wall of the apparatus.

DETAILED DESCRIPTION

The apparatus includes a mask 1 with a vaporizer 2. The mask also includes a bag 3 having an approximately cylindrical side and having a side 30 which is flattened so that it can be placed, like a bit, in the mouth 40 of the horse 4. On the upper part of the bag 3 there is provided a tightening belt 5, preferably having a conventional and not illustrated buckle arrangement, which partially grips around the bag 3 and extends with its free part 50 under the lower jaw 41 or the chin of the animal. Through this, the horse is prevented from opening its mouth, and is thus forced to breathe through its nose. At the same time, the bag 3 of the mask is held in the mouth of the horse. On the side of the bag 3 which is opposite the flattened side, and near the upper edge thereof, there is arranged a seal 31, made for example of soft rubber, which serves as a cushion. With this, the bag is supposed to rest tightly on the back of the nose of the horse and thus prevent on the one hand an escape of the inhalation medium from the bag, and on the other hand is supposed to reduce the pressure on the back of the nose of the horse.

Fastening of the bag 3 on the head of the horse 4 is further supplemented by a belt 6, which is secured to the upper edge 33 of the bag and is placed behind the ears and over the neck, and preferably has a conventional and not illustrated buckle arrangement. The belt can optionally be secured by an additional forehead or nose belt 60.

The bag 3 of the mask is preferably made of a flexible or stiff material which is impermeable to air. The bag has in its bottom a central portion or opening 32 which is permeable to gas, in front of which the vaporizer 2 is mounted. This vaporizer 2 is preferably a commercial product, for example the ultrasound inhalator discussed in Swiss Pat. No. 610 203, or can alternatively be a further product which is provided with an aerosol connection and is commonly used both in human and also in veterinary medicine.

If the bag is made of a flexible material, it can have longitudinally 34 or transversely 35 extending reinforcing ribs, so that it does not shrink during an inner underpressure and thus rest too closely on the covered part of the head of the animal, which would be uncomfortable for the animal.

The bag can have inlet 36 and outlet 37 valves, through which the introduction and discharge of the gaseous medium can be regulated. In particular, the valves are supposed to make possible on the one hand the ejection of exhaled air, and on the other hand are supposed to prevent the breathing in of a further gaseous media, for example cold ambient air.

For regulating more accurately the operation of a vaporizer 38, which includes a container containing an inhalation medium and having a cover 39 which can be opened and closed to control the release of the inhalation medium, a small rod operatively links the inlet valve 36 and cover 39 so that, during breathing in, the valve 36 opens cover 39 and thereby actuates the vaporizer 38 until valve 36 closes.

In a special embodiment, the bag can have at its upper edge and in the area of the flattened side an indentation 42, so that the edge of the bag also rests, after being introduced into the mouth, laterally on the head of the horse. The edge of the bag can, in the area of the indentation 42, namely at the point 44 which remains in the mouth of the animal and which has a lesser height h than the height H of the remaining part of the bag, be reinforced on the edge 43.

Compared with conventional inhalators, the inventive apparatus does not surround the entire head or nose of the animal but practically only the nostrils, while the mouth remains closed by the fastening arrangement for the mask.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an inhalation apparatus for an animal which includes a mask having means for facilitating inhalation and exhalation by an animal wearing said mask, and means for supplying to said mask a gaseous inhalation medium, the improvement comprising wherein said mask includes a bag which is open at an upper end thereof and has a cavity which communicates with said open upper end and is adapted to receive the nose of the animal, said open upper end of said bag terminating in a generally semi-cylindrical wall part and a flattened wall part extending across the concave side of said semi-cylindrical wall part, said semi-cylindrical wall part and said flattened wall part of said bag each terminating in an upper edge, said upper edges defining said open upper end of said bag, and wherein said mask includes an adjustable belt which extends around said bag, said belt having a first portion which is adjacent said semi-cylindrical wall part of said bag and a second portion which is spaced outwardly from said flattened wall part, said belt being spaced below said upper edge of said flattened wall part, whereby said flattened wall part can be placed in the mouth of the animal so that said bag receives the nose of the animal and the space between said second portion of said belt and said flattened wall part receives the lower jaw of the animal, and said adjustable belt can then be tightened until the animal is prevented from opening its mouth and must breathe through its nostrils.

2. The inhalation apparatus according to claim 1, wherein said semi-cylindrical wall part and said flattened wall part each have a lower edge opposite said upper edge thereof; wherein said bag defines a bottom wall part which extends between said lower edges of said semi-cylindrical and fattened wall parts, wherein said means for supplying to said mask a gaseous inhalation medium includes vaporizer means for producing a gaseous inhalation medium supported on the exterior surface of said bottom wall part of said bag, and wherein said bag is made of a flexible material which is generally impermeable to air except for a portion of said bottom wall part in the region of said vaporizer means which is gas permeable to permit the gaseous inhalation medium to flow from said vaporizer means to the inside of said bag.

3. The inhalation apparatus according to claim 2, wherein said vaporizer means is an ultrasound inhalator.

4. The inhalation apparatus according to claim 1, including an elongate holding belt which has two ends, each said end of said holding belt being connected to said upper edge of said semi-cylindrical wall part of said bag, said holding belt being adapted for placement over the back of the head of the animal.

5. The inhalation apparatus according to claim 1, wherein a resilient sealing cushion is supported on the interior surface of said semi-cylindrical wall part of said bag and extends along the entire length of said semi-cylindrical wall part adjacent said upper edge thereof, whereby said cushion can sealingly engage the nose of the animal.

6. The inhalation apparatus according to claim 1, wherein said bag has reinforcing rib means for preventing the collapse of said bag during an underpressure therein.

7. The inhalation apparatus according to claim 1, wherein said means for facilitating inhalation and exhalation includes said bag having inlet and outlet valve means for allowing fluid flow into and out of said bag, respectively.

8. The inhalation apparatus according to claim 7, wherein said means for supplying to said mask a gaseous inhalation medium includes said mask having vaporizer means for producing a gaseous inhalation medium supported on an exterior surface of said bag in the region of said inlet valve means, said vaporizer means including housing means defining a chamber in fluid communication with said inlet valve means and which can communicate with the interior of said bag through said inlet valve means, a vaporizer in said chamber, and means responsive to said inlet valve means for respectively actuating and deactuating said vaporizer as said inlet valve means opens and closes, respectively.

9. The inhalation apparatus according to claim 1, wherein said upper edge of said flattened wall part of said bag terminates below said upper edge of said semi-cylindrical part thereof, and wherein said flattened wall part of said bag has an indentation in said upper edge thereof.

* * * * *

UNITED STATES PATENT AND TRADEMARK OFFICE

CERTIFICATE OF CORRECTION

PATENT NO. : 4 546 768

DATED : October 15, 1985

INVENTOR(S) : Georg FEIERABEND

It is certified that error appears in the above-identified patent and that said Letters Patent is hereby corrected as shown below:

On the title page; change the name of the inventor from "Georg Ferierabend" to ---Georg Feierabend---.

Signed and Sealed this

Fourteenth Day of October, 1986

[SEAL]

*Attest:*

DONALD J. QUIGG

*Attesting Officer* *Commissioner of Patents and Trademarks*